(12) United States Patent
Pearce, III et al.

(10) Patent No.: US 8,093,040 B2
(45) Date of Patent: Jan. 10, 2012

(54) METHOD FOR GROWING BACTERIA

(75) Inventors: Robert Clarence Pearce, III, Arlington, TX (US); Dale V. Kiplinger, Carrollton, TX (US); Jose E. Evaro, Mansfield, TX (US); Judith Gayle Pruitt, Mesquite, TX (US); Joseph Thomas Colarusso, Arlington, TX (US)

(73) Assignee: NCH Corporation, Irving, TX (US)

( * ) Notice: Subject to any disclaimer, the term of this patent is extended or adjusted under 35 U.S.C. 154(b) by 218 days.

(21) Appl. No.: 12/644,785

(22) Filed: Dec. 22, 2009

(65) Prior Publication Data

US 2010/0099165 A1    Apr. 22, 2010

Related U.S. Application Data

(60) Division of application No. 11/282,785, filed on Nov. 18, 2005, now Pat. No. 7,635,587, which is a continuation of application No. 10/636,339, filed on Aug. 7, 2003, now Pat. No. 7,081,361.

(51) Int. Cl.
*C12M 1/36* (2006.01)
*C12Q 3/00* (2006.01)

(52) U.S. Cl. ... 435/286.5; 435/3; 435/286.7; 435/289.1; 435/309.2; 435/813

(58) Field of Classification Search ............... 435/286.5, 435/286.7, 289.1, 309.2, 813
See application file for complete search history.

(56) References Cited

U.S. PATENT DOCUMENTS

| 4,244,815 | A | 1/1981 | Chaikin et al. |
| 4,426,450 | A | 1/1984 | Donofrio |
| 4,888,294 | A | 12/1989 | Van Wezel et al. |
| 5,350,543 | A | 9/1994 | Spradley |
| 5,369,032 | A | 11/1994 | Pratt |
| 5,447,866 | A | 9/1995 | Runyon |
| 5,525,301 | A | 6/1996 | Newberg et al. |
| 5,654,197 | A | 8/1997 | Jem et al. |
| 5,739,031 | A | 4/1998 | Runyon |
| 6,168,949 | B1 | 1/2001 | Rubenberger |
| 6,335,191 | B1 | 1/2002 | Kiplinger et al. |
| 7,081,361 | B2 * | 7/2006 | Pearce et al. ............... 435/286.5 |
| 7,635,587 | B2 * | 12/2009 | Pearce et al. ............... 435/286.5 |

* cited by examiner

*Primary Examiner* — William H Beisner
(74) *Attorney, Agent, or Firm* — Locke Lord, LLP

(57) ABSTRACT

A biomass generator useful for continuously growing and withdrawing bacteria to be used in a desired beneficial application, the generator having a bacteria growth chamber; water and nutrient inlet ports; upper and lower outlet ports; a recirculating pump withdrawing and reintroducing fluid to establish a vortex in the growth chamber while controlling foaming and pump cavitation; a low pressure air inlet line discharging air inside the growth chamber above the vortex; a fluid discharge line receiving bacteria-containing fluid from the upper outlet port of the growth chamber; a flush line discharging wash water into the fluid discharge line; and an electrical controller cooperating with solenoid-operated valves and a feeder mechanism to periodically introduce water and nutrients into the chamber, thereby simultaneously causing bacteria-containing fluid to be discharged from the growth chamber through the upper outlet port. A method for growing bacteria using the subject apparatus is also disclosed.

17 Claims, 7 Drawing Sheets

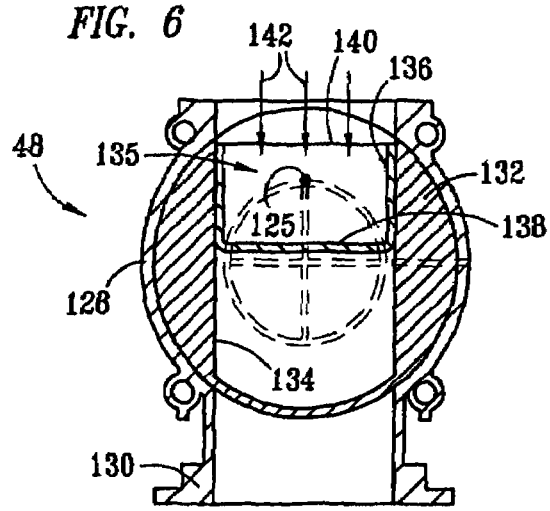
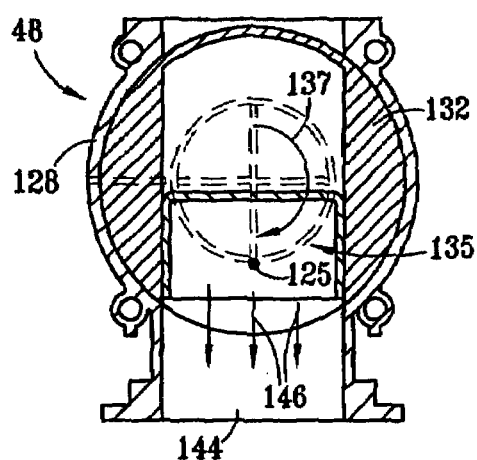
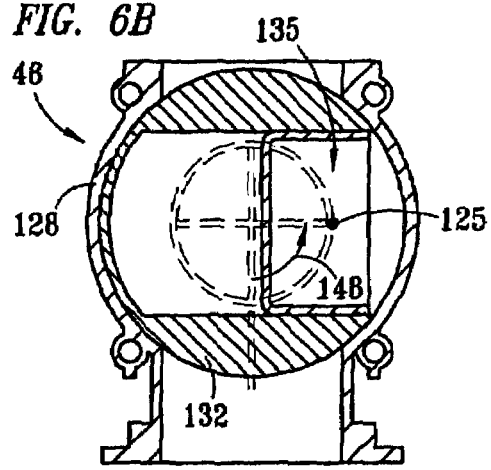
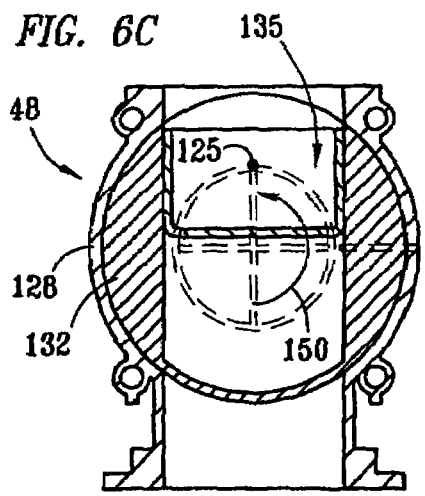

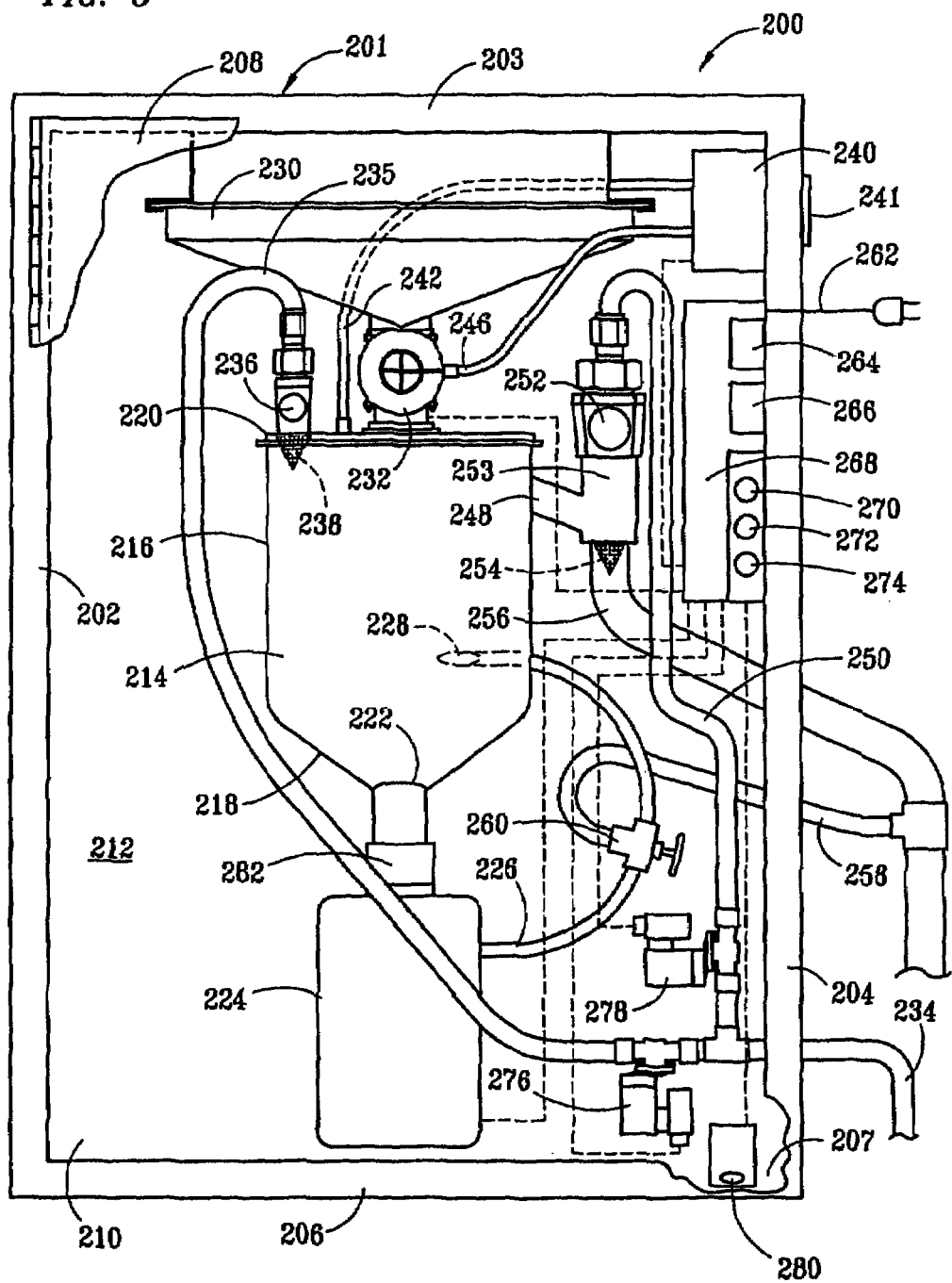

METHOD FOR GROWING BACTERIA

CROSS-REFERENCE TO RELATED APPLICATIONS

This application is a divisional of U.S. application Ser. No. 11/282,785, now issued as U.S. Pat. No. 7,635,587, which is a continuation of U.S. application Ser. No. 10/636,339, filed Aug. 7, 2003, now U.S. Pat. No. 7,081,361.

BACKGROUND OF THE INVENTION

1. Field of the Invention

This invention relates to apparatus and an automated method for growing and harvesting aerobic bacteria for use in various beneficial industrial, agricultural, environmental and commercial applications.

2. Description of Related Art

Previously known systems for growing aerobic bacterial strains are disclosed, for example, in U.S. Pat. Nos. 4,244,815; 4,426,450; 4,888,294; 5,350,543; 5,447,866; 5,654,197; 6,168,949 B1 and 6,335,191 B1.

One preferred prior art system that is useful for growing aerobic bacterial strains having desired beneficial uses is disclosed in U.S. Pat. No. 6,335,191 B1. In that system, bacteria are grown by an automated batch process and are discharged periodically, most preferably once daily, into a drain or collection vessel. Other prior art systems and apparatus for growing bacteria are disclosed, for example, in the prior art cited in U.S. Pat. No. 6,335,191 B1.

Notwithstanding the benefits and advantages achievable through use of the previously known systems and devices, there remains a need for a relatively uncomplicated, inexpensive and reliable, continuous flow biomass generator that can operate for days or weeks without attention or operator intervention. Such an apparatus and method will preferably facilitate the rapid growth of aerobic bacteria without excessive foaming that is frequently encountered when using prior art biomass generators. Many prior art devices either bubble pressurized air into the growth chamber below the liquid surface or use a pressurized stream of recirculated liquid flowing through an eductor to draw fresh air into the stream, which is then injected back into the bacteria growth chamber. Neither of these types of prior art devices is believed to be satisfactory for growing and harvesting large bacterial yields without excessive foaming as is possible through use of the apparatus and method of the invention.

SUMMARY OF THE INVENTION

One preferred embodiment of the invention disclosed herein is a continuous flow biomass generator that is useful for continuously growing and withdrawing bacteria for real time or subsequent use in a desired beneficial application. This embodiment of the subject biomass generator has a bacteria growth chamber; water and nutrient inlet ports; a nutrient feed mechanism; an air inlet line; a recirculating pump withdrawing fluid from an outlet in the bottom of the growth chamber and reintroducing it tangentially to establish a vortex in the growth chamber; a fluid discharge line continuously withdrawing bacteria-containing fluid from the growth chamber; and a flush line discharging wash water into the fluid discharge line. The biomass generator of the invention does not have a mechanical stirring device disposed inside the growth chamber and does not introduce fresh air into the growth chamber below the surface of the bacteria-containing liquid.

Another preferred embodiment of the invention is a method for using the continuous flow biomass generator described above to grow and harvest bacteria. The method desirably comprises the steps of establishing a starter medium of potable water, starter bacteria and nutrient inside the bacteria growth chamber; continuously withdrawing, recirculating and re-injecting a portion of the medium tangentially into the growth chamber to establish a vortex, continuously injecting low pressure air into the growth chamber above the vortex; continuously adding water to the growth chamber through a control valve or pressure regulator by gravity flow at a controlled, low flow rate relative to the flow rate being recirculated into the growth chamber; continuously harvesting bacteria from the growth chamber and flushing it down a bacteria harvesting line; and periodically replenishing bacteria nutrient in the growth chamber. The water used to flush harvested bacteria down the bacteria harvesting line is desirably an excess or overflow from the water that is being controllably introduced into the growth chamber.

Another preferred embodiment of the invention as disclosed herein is a biomass generator that utilizes pulsed periodic introduction of water into the growth chamber in combination with associated periodic harvesting of bacteria that grows continuously inside the chamber. The apparatus used in this embodiment of the invention is similar to that disclosed in the method embodiment above but differs in several significant ways. First, the pulsed flow of water into the growth chamber is controlled by a timer-driven solenoid valve. Second, the bacteria harvesting line used to harvest bacteria from the growth chamber is periodically flushed with water supplied through a second timer-driven solenoid valve, which is activated coincidentally with or shortly following the pulsed introduction of water. Third, an additional air line is provided to dry the feed mechanism between uses, thereby preventing undesirable bacterial buildup within the feed mechanism. Fourth, a float valve is provided in the bottom of the cabinet containing the subject biomass generator to facilitate automatic shutdown of the system whenever liquid accumulates in the bottom of the cabinet due to failure of any mechanical or electrical component of the apparatus. Fifth, push buttons are provided to manually initiate various operations of the apparatus independently of the timers and electronic controller. Sixth, a manually controlled valve is provided in the fluid recirculation loop between the recirculating pump and the growth chamber to facilitate draining and flushing the growth chamber during occasional shutdowns of the apparatus.

Another preferred embodiment of the invention, described herein in relation to the biomass generator embodiment that utilizes pulsed periodic introduction of water into the growth chamber in combination with associated periodic harvesting of bacteria that is grown continuously inside the chamber, is a method for growing bacteria comprising the steps of introducing water, starter bacteria and nutrient into a growth chamber; continuously withdrawing bacteria-containing liquid medium through an orifice element disposed in the bottom of growth chamber; recirculating the withdrawn medium through a pump and back into the growth chamber, reintroducing the recirculated liquid medium substantially tangentially into the liquid inside the growth chamber to form a vortex inside the growth chamber; aerating the liquid medium inside the growth chamber by introducing low pressure air into the growth chamber above the vortex while controlling foaming; periodically introducing additional water into the growth chamber; periodically harvesting bacteria-containing liquid medium from the growth chamber and flushing the harvested medium into a receiving vessel or flow line; and periodically dispensing additional nutrient into the growth chamber.

According to another preferred embodiment of the invention, a biomass generator is disclosed that comprises a cabinet having a bacteria growth chamber, nutrient feeder mechanism and recirculating pump disposed inside, the cabinet being partitioned into first and second sections so that the bacteria growth chamber and recirculating pump are thermally insulated from each other. According to another particularly preferred embodiment of the invention, that portion of the cabinet containing the growth chamber is temperature-controlled.

Bacteria grown inside the biomass generator of the invention can be harvested for immediate use or stored for subsequent use as desired. The apparatus and method of the invention are especially effective for growing bacteria for a particular application at or near a preferred use site. The self-contained system of the invention can be installed inside a lockable cabinet for access only by authorized personnel. Because the cabinet can be wall mounted, no floor space is required to install the system, and the only required utilities are a water supply and a conventional 110 volt electrical outlet. Unlike systems disclosed in the prior art, the apparatus and method disclosed herein enable the user to achieve rapid growth of a selected strain of helpful bacteria by providing excellent aeration and temperature control without excessive foaming and without pump cavitation that is detrimental to long term service.

Because the apparatus and method of the invention are adapted to sustain continuous bacterial growth over long periods, the resultant bacteria can be utilized in applications where continuous or periodic replenishment is necessary, or in applications where the live bacteria are stored in a suitable, life-sustaining collection vessel pending use. The apparatus requires only periodic servicing to replenish the nutrient material in the feed storage hopper and occasional shutdowns for general inspection, cleaning and maintenance.

BRIEF DESCRIPTION OF THE DRAWINGS

The apparatus of the invention is further described and explained in relation to the following figures of the drawings wherein:

FIG. 6 is an enlarged cross-sectional elevation view of the lower portion of a preferred nutrient feeder mechanism for use in the invention, taken along line 6-6 of FIG. 3 and showing the feed cup in the upright receiving position;

FIG. 6A is the preferred nutrient feeder mechanism of FIG. 6, but showing the feed cup rotated downwardly to the inverted discharge position;

FIG. 6B is the preferred nutrient feeder mechanism of FIG. 6, but showing the feed cup rotated upwardly to the intermediate standby position;

FIG. 6C is the preferred nutrient feeder mechanism of FIG. 6, with the feed cup again rotated upwardly from the standby position to the receiving position of FIG. 6;

FIG. 8 is a front elevation view, partially broken away, of another preferred embodiment of the continuous flow biomass generator of the invention.

DESCRIPTION OF THE PREFERRED EMBODIMENTS

Figure 1:
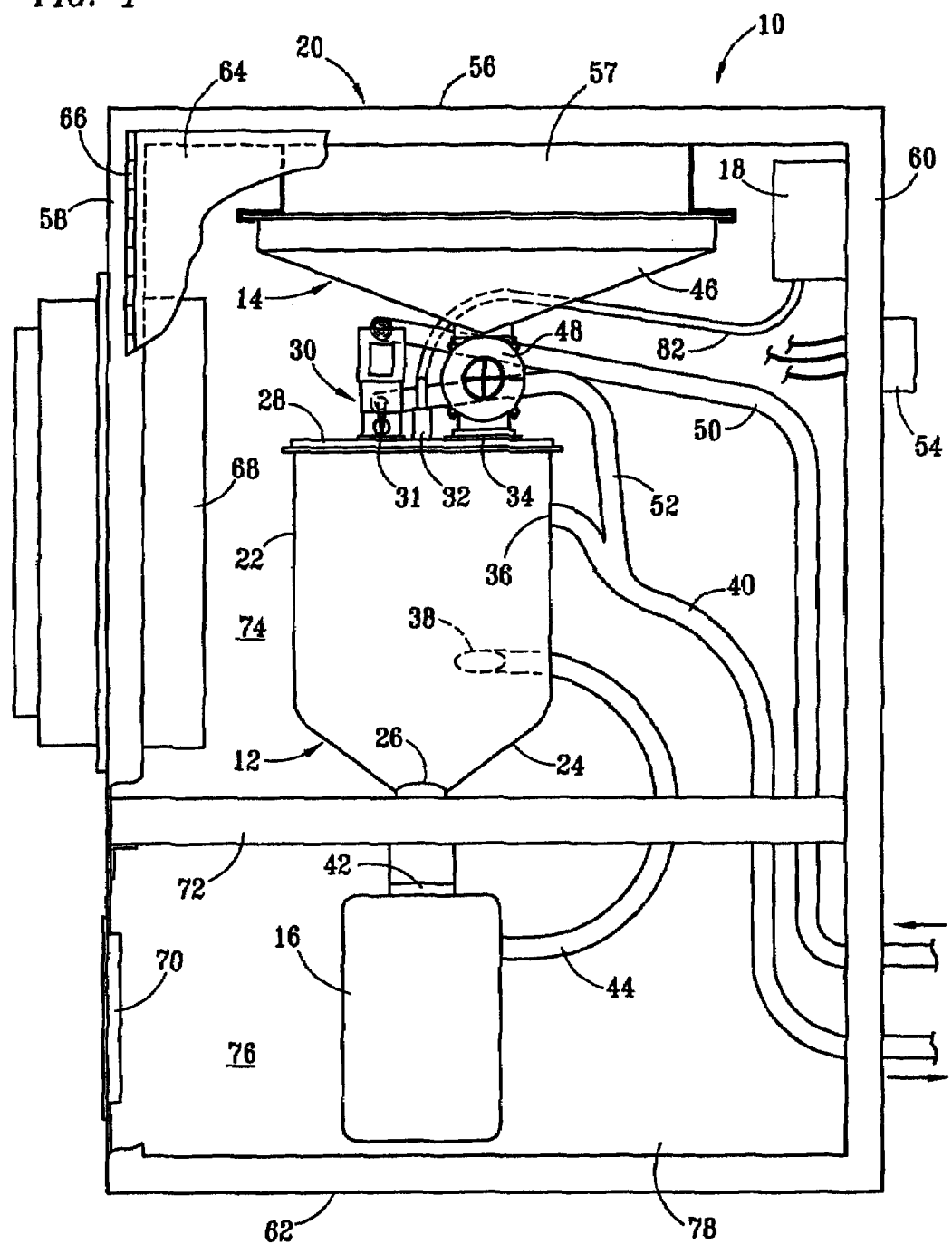
FIG. 1 is a front elevation view, partially broken away, of a preferred embodiment of the continuous flow biomass generator of the invention.
Figure 2:
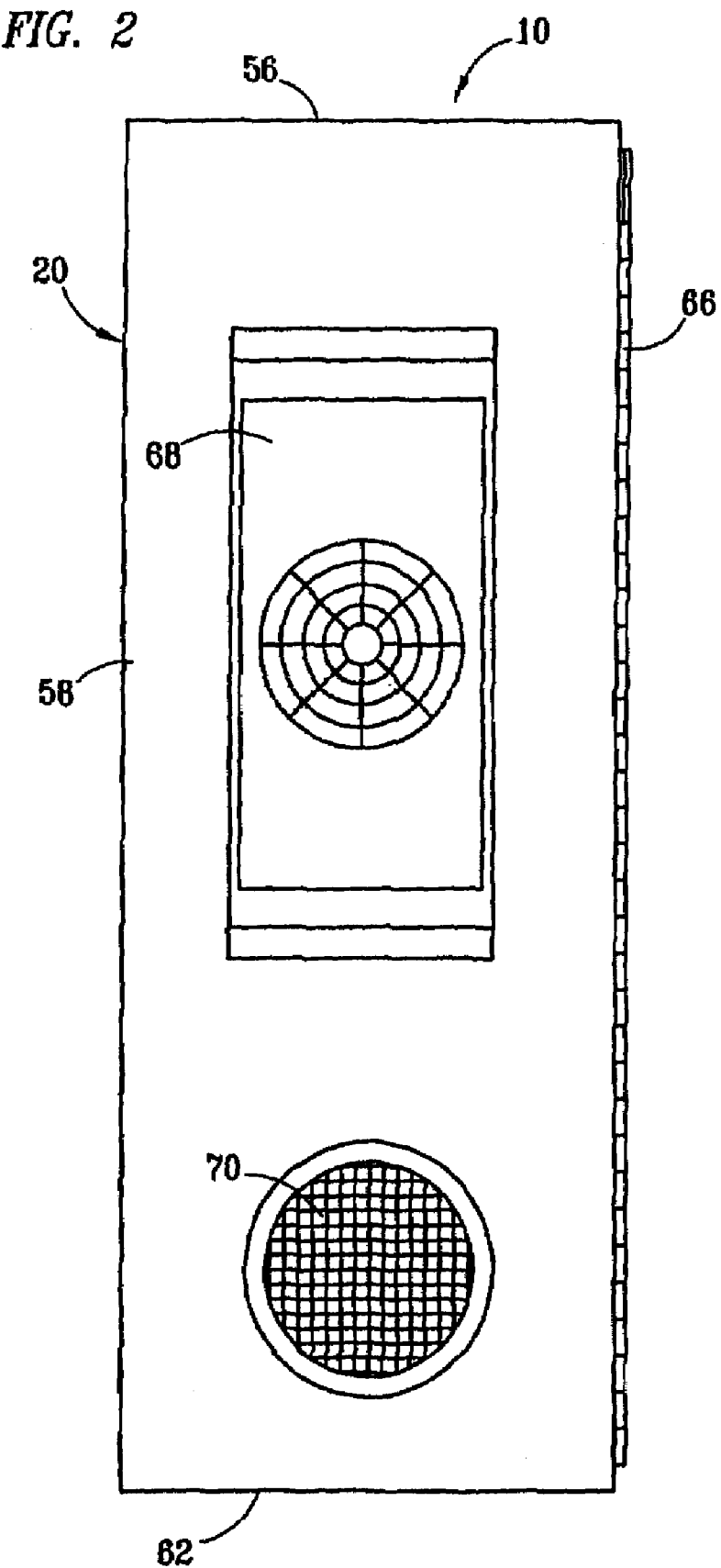
FIG. 2 is a left side elevation view of the continuous flow biomass generator of FIG. 1.
Figure 3:
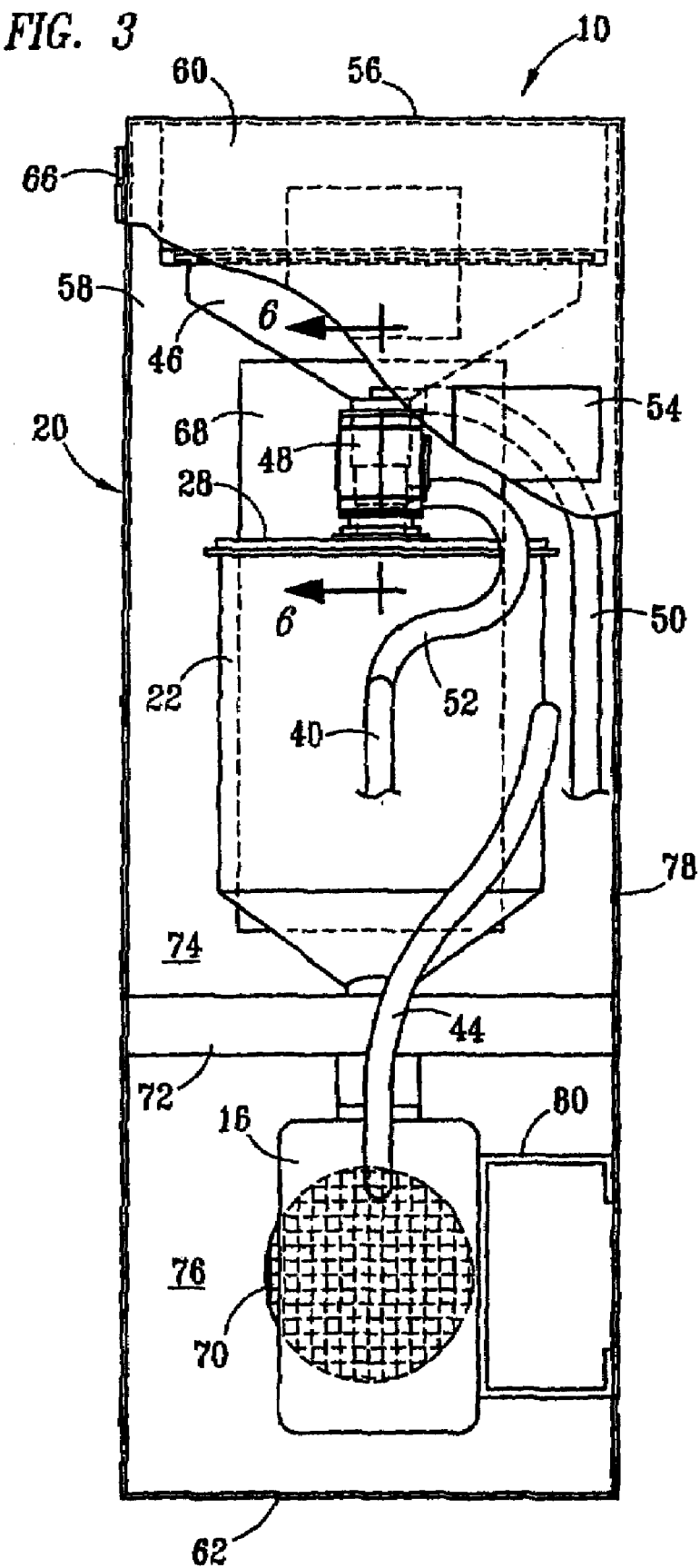
FIG. 3 is a right side elevation view, partially broken away, of the continuous flow biomass generator of FIGS. 1 and 2.

Referring to FIGS. 1-3, biomass generator 10 of the invention preferably comprises bacteria growth chamber 12, feeder mechanism 14, recirculating pump 16 and air pump 18 disposed inside cabinet 20. Cabinet 20 preferably further comprises top wall 56, back wall 57, side walls 58, 60, bottom wall 62 and door 64. Door 64 is preferably attached to cabinet 20 by hinge 66 to permit easy access to first and second interior sections 74, 76, which are separated by thermal insulation panel 72. Although not shown in the drawings, a lock or cable seal can be provided to prevent unauthorized tampering with the contents of cabinet 20 during use. According to one preferred embodiment of the invention, bacteria growth chamber 12 is made of a translucent polymeric container having an attachable cover 28. The volume of bacteria growth chamber 12 is preferably about 3 liters, although it will be appreciated that larger and smaller growth chambers can likewise be used within the scope of the invention. Cabinet 20 is preferably made of sheet metal, although other similarly effective materials such as fiberglass or the like can be used.

Temperature control unit 68 is preferably disposed in side wall 58, communicates with first interior section 74, and is powered by 110 volt AC current. Vent 70 is desirably provided in one of side walls 58, 60 to ventilate second interior section 76 containing recirculating pump 16, and it will be appreciated that a plurality of vents or a vent in combination with a small exhaust fan (not shown) can be utilized to provide cross-ventilation inside second interior section 76 if desired. The use of a thermal insulation panel 72 between bacteria growth chamber 12 and recirculating pump 16 is also preferred to help prevent overheating in the interior of cabinet 20. This is particularly desirable where recirculating pump 16 generates significant heat or where the interior of cabinet 20 otherwise reaches temperatures higher than those preferred for sustained, rapid bacterial growth. Depending upon the use environment and ambient temperatures, temperature control unit 68 may not be required to maintain the temperature of bacteria growth chamber 12 within a desired range. Although the preferred temperature range for sustaining rapid bacterial growth can vary according to factors such as the type of bacteria, etc., a temperature range of from about 16 to about 40° C. (about 60 to about 104° F.), and most preferably from about 29 to about 32° C. (about 84 to about 90° F.), is generally beneficial inside the cabinet section where bacteria growth chamber 12 is located.

Bacteria growth chamber 12 preferably further comprises cylindrical sidewall 22, conical bottom wall 24 extending from the bottom of sidewall 22 to a centrally disposed outlet port 26, and cover 28 comprising water, air and nutrient inlet ports 31, 32, 34, respectively. During operation of the apparatus, water is introduced continuously into bacteria growth chamber 12 through inlet port 31 by inlet flow control device 30, as described in greater detail below. Inlet flow control device 30 receives water from water supply line 50, which is preferably connected to a pressurized water source (not shown) outside cabinet 20. Low pressure air is introduced continuously into bacteria growth chamber 12 through inlet port 32 from air hose 82 connected to air pump 18. Air pump 18 desirably delivers to bacteria growth chamber 12 a sufficient supply of air to support rapid bacterial growth at a pressure sufficient to enter growth chamber 12 without disrupting the vortex created inside the growth chamber, as discussed below, and without causing Nutrient material, preferably in the form of pellets, selected to promote growth of the bacteria being cultivated is introduced into bacterial growth chamber 12 through inlet port 34 from feed storage hopper 46 by feed metering device 48. Such nutrient material is preferably introduced in the form of pellets because of their tendency to sink into fluid 84 inside growth chamber 12. Powder and liquid nutrients are not preferred because of the greater likelihood they might float on the surface and be discharged through line 40 with the harvested bacteria-containing fluid.

Figure 4:
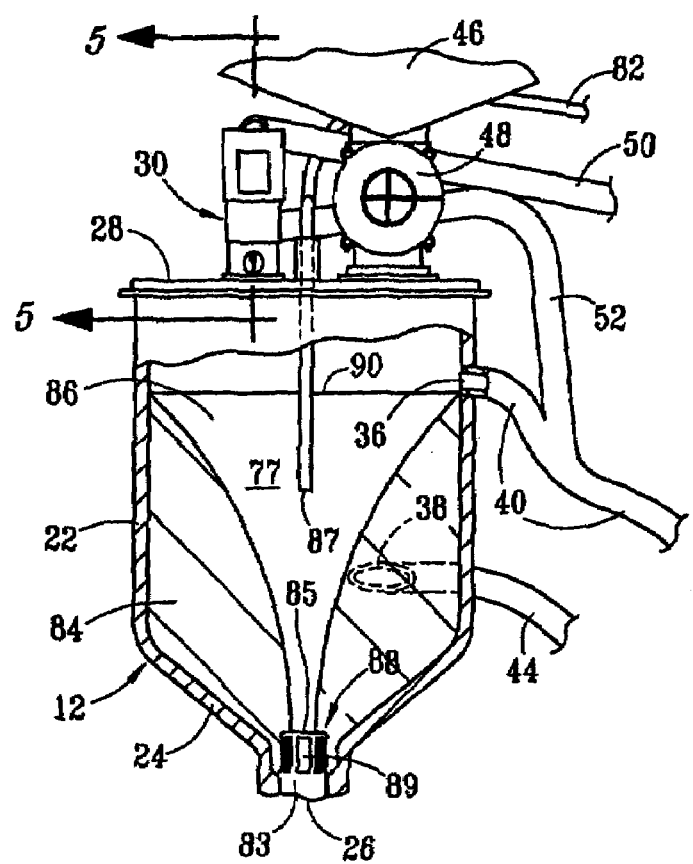
FIG. 4 is a front elevation view, partially broken away and partially in cross-section, showing the inside of the growth chamber of the continuous flow biomass generator of the invention.

Inlet 42 of recirculating pump 16 is connected in fluid communication with outlet 26 of bacteria growth chamber 12, and fluid outlet line 44 directs pressurized fluid discharged from the outlet of pump 16 back into the lower portion of bacteria growth chamber 12, preferably at a point slightly above the bottom of side wall 22. Recirculating fluid outlet port 38 at the discharge end of line 44 is preferably configured to discharge the recirculated fluid tangentially inside side wall 22 to promote the formation of a vortex as further described below. Fluid discharge line 40 communicates with the interior of bacteria growth chamber 12 through discharge port 36 that, as seen in FIG. 4, is disposed proximal to the uppermost liquid level inside bacteria growth chamber 12. As the liquid level inside bacteria growth chamber 12 rises with the introduction of water through inlet port 31, bacteria-containing fluid is continuously withdrawn through discharge port 36 and is desirably flushed downwardly through fluid discharge line 40 by flush water flowing into discharge line 40 from flush water line 52.

Referring to FIG. 4, the forwardly extending portion of side wall 22 and bottom wall 24 are broken away to reveal the interior of bacteria growth chamber 12 and vortex breaker element 88 disposed in outlet 26 in the center of the downwardly sloping bottom wall. The principal function of vortex breaker element 88 is to help maintain the stability of vortex 77 and to prevent air inside the lower end of vortex 77 from being drawn downwardly through outlet port 26 into inlet 42 of recirculating pump 16, thereby protecting pump 16 from cavitation. Pump cavitation can accelerate wear on the surface of the pump impeller and also contribute to undesirable "slug flow" in which large pockets of air are disposed between discrete volumes of liquid inside outlet line 44, causing irregular flow that disturbs the vortex and contributes to the undesirable formation of foam when the slugs reenter growth chamber 12. Pump 16 is preferably powered by a motor operating at 24 volts AC or 12 volts DC. Where the volume of bacteria growth chamber 12 is about 3 liters, pump 16 is desirably rated so as to provide a recirculation rate of about 15 to 23 liters (4 to 6 gallons) per minute.

According to one embodiment of the invention, vortex breaker element 88 is a generally cylindrical body having a top end wall 85, a cylindrical side wall 83, and a plurality of orifices 89 that are circumferentially spaced around side wall 83 to permit the passage of liquid 84 through them. The size, shape and number of orifices 89 can be varied within the scope of the invention, although the combined area of the openings is most desirably approximately equal to the cross-sectional area of outlet port 26 so as not to overly restrict the flow of fluid 84 into pump inlet 42, thereby "starving" recirculating pump 16. If desired, a small orifice can also be provided in top end wall 85 of vortex breaker element 88. Orifices 89 are desirably each small enough to prevent prills or pellets of starter bacteria or nutrient from exiting growth chamber 12 through outlet port 26 until they are substantially dissolved in fluid 84. It will be appreciated that vortex breaker elements 88 having different shapes and configurations can likewise be used in the apparatus and method of the invention, provided that such other elements also serve to prevent the vortex from being drawn into pump inlet 42 without starving pump 16.

As seen in FIG. 4, air inlet line 82 preferably terminates at tip 87 disposed in the air cavity formed by vortex 77 within fluid 84 in order to provide oxygen directly to vortex 77. Tip 87 is preferably disposed about 3.8 cm (1.5 inches) below the resting level of liquid 84 inside growth chamber 12 before recirculation pump 16 is activated, and will remain above liquid surface level 86 after pump 16 is activated so that tip 87 is disposed inside vortex 77 and is not covered by liquid 84 during continuous operation of the invention. Air pump 18 desirably maintains a positive pressure of about 0.5 pisg inside bacteria growth chamber 12 to help prevent undesirable bacteria from gaining entry into and becoming established inside the chamber. Where bacteria growth chamber 12 has an interior volume of about 3 liters, air pump 18 and inlet air line 18 are preferably sized to provide an air flow rate of from about 2 to about 6 liters per minute.

Figure 5:
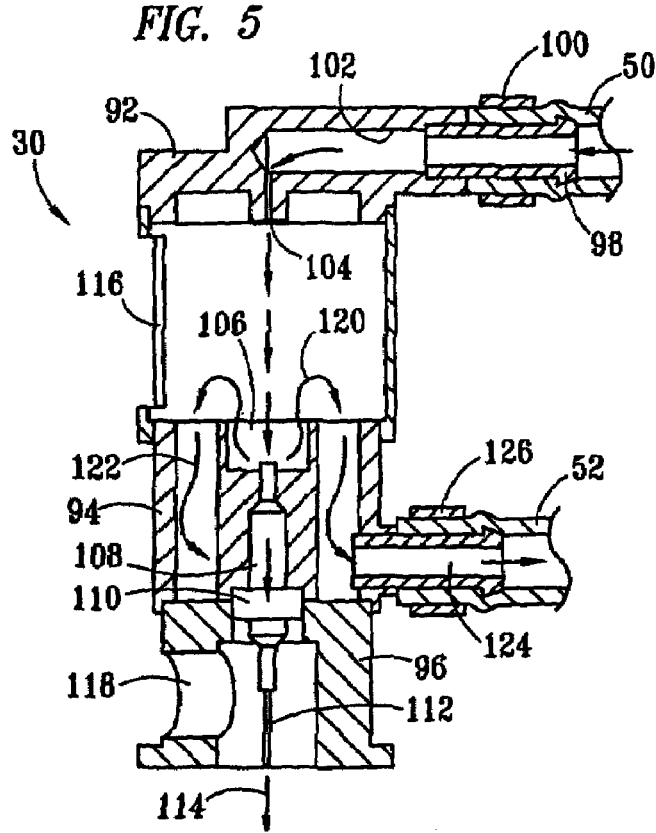
FIG. 5 is an enlarged cross-sectional elevation view of a preferred water flow control mechanism for use in the invention, taken along line 5-5 of FIG. 4.

The structure and operation of one preferred water inlet flow control device 30 is further described and explained in relation to FIG. 5 of the drawings. Water is desirably supplied to inlet passage 102 of device 30 through water inlet line 50, which can be attached to device 30 using hose barb 98 and clamp 100, or by conventional fittings, or by any other similarly effective means. Water supplied to flow control device 30 can be pretreated if desired, such as by a filter, water softener, or the like, although such pretreatment is not believed to be required where the inlet water source is a potable water supply. Inlet flow control device 30 preferably functions as both a flow controller and pressure controller, most preferably dropping the pressure and flow rate in two stages. Inlet flow control device 30 further comprises head 92, body 94 and base 96. Base 96 is preferably attachable to the top of cover 28 of growth chamber 12 as seen in FIGS. 1 and 4. Water entering inlet passage 102 flows downwardly through smaller diameter passage 104 in head 92 and falls by gravity past viewing window 116, and into well 106 in body 94. The vertical distance between the bottom of passage 104 and the top of well 106 must be at least one inch to comply with plumbing codes requiring a one inch air gap as a backflow preventer. The diameter of passage 104 is preferably such that water falls either at a fast drip or in a small stream into well 106. The flow rate is preferably such that more water accumulates in well 106 than is needed to supply growth chamber 12 during continuous operation. Some of the water flows downwardly through bore 108 of needle valve 110 positioned inside body 94 and base 96, and surplus water accumulates in well 106 until it flows over the top into annulus 122 of body 94, as indicated by arrows 120. Water flowing downwardly from well 106 through needle valve 110 falls as droplets or thin stream 112 past viewing port 118 in base 96. Stream 112 is desirably aligned with inlet port 31 of cover 28 of growth chamber 12, as seen in FIG. 1, so that stream 112 falls onto surface 86 of fluid 84.

Surplus water flowing into annulus 122 passes through outlet passage 124 into flush line 52, which is illustrated as being secured to device 30 by clamp 126. It will be apparent that the water flow rate through passage 104 must be sufficiently greater than the water flow rate through needle valve 110 to provide the surplus water needed for flush line 52. Unless fluid discharge line 40 is flushed continuously by water flowing through flush line 52, there is a greater likelihood that bacteria can be stranded on the walls of fluid discharge line 40 instead of being transported to the use site or an accumulation vessel as desired.

Figure 7:
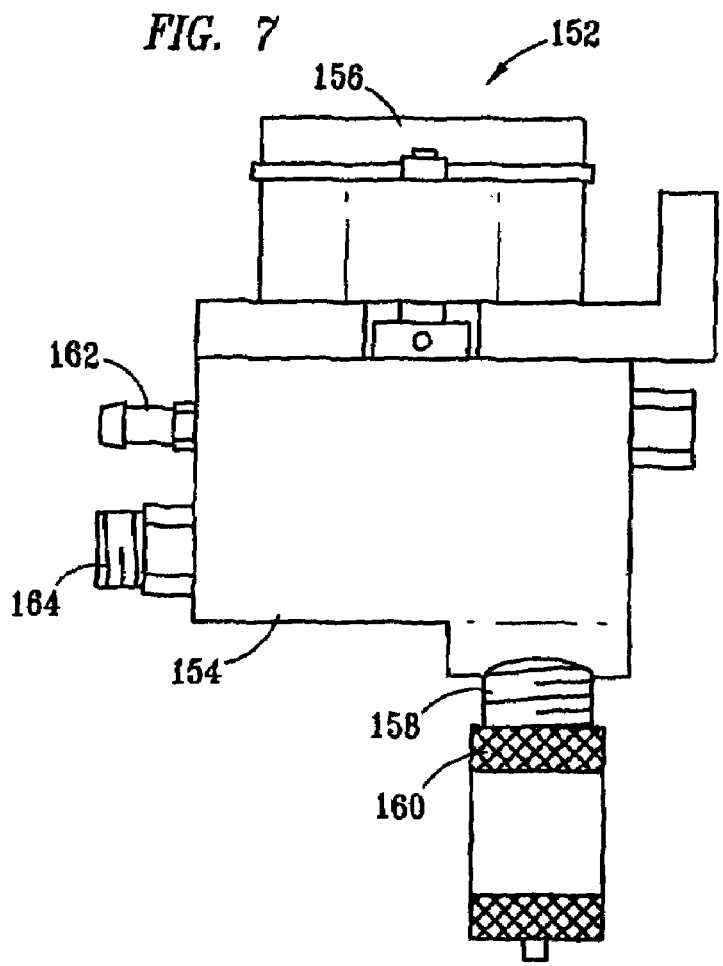
FIG. 7 is a simplified front elevation view of an alternate water flow control device suitable for use in the biomass generator of the invention.

Another water inlet device 152 suitable for use in the apparatus of the invention is disclosed and described in relation to FIG. 7. Referring to FIG. 7, device 152 is preferably attachable to cabinet 20 as previously described in relation to FIGS. 1 through 3. Device 152 is a piston operated, positive displacement inlet device driven by a synchronous 60 cycle timer motor. Inlet water received through inlet port 162 from an outside source is delivered to outlet port 164 at a rate that is controlled by manual rotation of adjustment knob 160 and threaded linkage 158 to selectively adjust the displacement of a cylinder disposed inside body 154. The piston, not visible in FIG. 7, is powered by synchronous motor 156 mounted on body 154. Outlet port 164 is preferably connected to inlet port 31 in cover 28 of growth chamber 12 by a flexible polymeric flow line not shown in FIG. 5. Where flow control device 152 is used to supply water to growth chamber 12, a separate needle valve (not shown) disposed upstream of device 152 is desirably used to supply water to flush line 52.

It will be appreciated upon reading this disclosure that other similarly effective water inlet devices can also be used in the apparatus and method of the invention. With this embodiment of the invention, during normal operation the daily inlet water flow into chamber 12 and the daily outlet flow of fluid 84 from chamber 12 will preferably be approximately equivalent to from about one-third to about one-half the volume of the chamber. It should be appreciated, however, that this amount can vary according to the bacteria concentration and growth rate, which are in turn dependent upon various factors such as the bacteria type, the amount and type of nutrient, the temperature inside bacteria growth chamber 12 and the oxygen level inside fluid 84. According to one preferred embodiment of the invention, the water flow rate into bacteria growth chamber 12 during steady-state operation is about 1.6 liters per day, meaning that an approximately equivalent amount of water will be discharged each day through fluid discharge line 40. In order to keep bacteria discharged from discharge port 36 flushed out of discharge line 40, the flow rate through flush line 52 will preferably range from about 2 to about 20 liters (from about 0.5 to about 5 gallons) per day.

The structure and operation of a preferred feed metering device 48 of feeder mechanism 14 is further described and explained in relation to FIGS. 6 and 6A-6C. Referring first to FIG. 6, feed metering device 48 preferably comprises base member 130 attachable to cover 28 of growth chamber 12 (FIG. 4), and housing 128 having a horizontally disposed, generally cylindrical bore comprising rotatably mounted core member 132 with a transverse cylindrical bore 134 extending substantially through the core. Feed cup 135 having cylindrical side wall 136 bounded by bottom wall 138 and top edge 140 is disposed in stationary relation to core member 132 during use. A low voltage DC motor disposed behind the cylindrical bore of housing 128 (visible in FIG. 3) comprises a gear drive connected by pin 125 to core member 132. Pin 125 is adapted to rotate core member 132 and feed cup 135 to a desired angular position relative to housing 128 upon receipt of a signal from preprogrammed electronic controller 54. The diameter and volume of feed cup 135 are desirably such that feed cup 135 will receive a desired amount of nutrient feed by gravity flow from feed storage hopper 46 (FIG. 1) whenever core member 132 is rotated by pin 125 to the point on circle 127 where top edge 140 of feed cup 135 is in the upright position.

It should be understood that the preferred diameter and depth of feed cup 135 and the diameter of the discharge port on the underside of feed storage hopper 46 can vary, depending upon the amount of nutrient feed desired and upon the particle size and shape of the nutrient feed, recognizing that different types of particulate matter have different aspect ratios and different tendencies to bridge across openings through and into which they are discharged by gravity flow. According to a particularly preferred embodiment of the invention, commercially available food pellets are periodically loaded into hopper 46, which can be constructed so as to easily slide in and out of cabinet 20 whenever biomass generator 10 is routinely serviced. Where bacteria growth chamber 12 has a volume of about 3 liters, about 29 grams of nutrient are preferably introduced into chamber 12 daily, in four equal increments of about 7.25 grams each, with each increment being introduced approximately 6 hours apart. Feed cup 135 should therefore have a volume that will accommodate up to about 7.5 grams of nutrient.

FIGS. 6A-6C depict the same structure, except that pin 125, core member 132 and feed cup 135 are rotated to different angular positions relative to body 128. In FIG. 6A, feed cup 135 has been rotated to the right and downwardly through an angle of 180 degrees as indicated by arrow 137. Feed cup 135 is in a fully inverted position where any nutrient feed particles contained inside cup 135 are discharged by gravity through outlet port 144 of base 130, as indicated by arrows 146, and through feed inlet port 34 of cover 28 into growth chamber 12 (seen in FIG. 1). In FIG. 6B, feed cup 135 is rotated back to the 90 degree position as indicated by arrow 148, where it remains until the beginning of the next feed cycle. Feed cup 135 is desirably stored in the 90 degree position so that the open end of feed cup 135 is covered and protected. If feed cup 135 rests in the upright position between feedings, moisture picked up during discharge over growth chamber 12 can cause pellets to soften and clump. If feed cup 135 rests in the downwardly directed position between feedings, bacterial buildup on the feed cup can occur. In FIG. 6C, feed cup 135 is again rotated to the position as shown in FIG. 6 for refilling with nutrient feed.

A preferred embodiment of the method of the invention is further described and explained in relation to FIGS. 1-6. Referring first to FIGS. 1 and 4, during start-up of the apparatus, approximately 1.6 liters of water are introduced into growth chamber 12 to achieve an initial fill level below the level of discharge port 36. The beginning quantity of water will of course depend upon the interior volume of chamber 12 and upon the drip rate at which fresh water enters the chamber. The initial fill level should be sufficiently below discharge port 36 that starter bacteria and nutrient can be added, so that a vortex can be formed when recirculation is started, and so that the apparatus can be run for several hours thereafter without accidentally discharging any significant amount of bacteria-containing fluid. During this time, the starter bacteria will reach a desired growth population or concentration. As the starter bacteria is given time to grow and multiply, the make-up water entering growth chamber 12 through inlet control device 30 will gradually raise the highest liquid level 90 to the level of discharge port 36.

The beginning quantity of water can be introduced slowly through inlet flow control device 30 or, preferably, is introduced more rapidly by removing cover 28 and pouring water into chamber 12, or by inserting a hose through inlet port 31 prior to placement of flow control device 30, or into another resealable port (not shown) provided for that purpose. The beginning water is preferably introduced into chamber 12 at a temperature conducive to bacterial growth, or is permitted to equilibrate to such a temperature prior to introducing starter bacteria and nutrient. If desired, the beginning quantity of water can be introduced at ambient temperature and, if too cold, can be heated using temperature controller 68 or by recirculating it through pump 16 until the temperature reaches a desired level, generally between about 16 and 26° C. (about 60 to about 80° F.). During sustained, continuous operation of biomass generator 12, the temperature will preferably range between about 16 and about 40° C. (about 60 to about 104° F.), and most preferably between about 29 and about 32° C. (about 84 to about 90° F.) to promote bacterial growth.

Whenever the water temperature reaches a level adequate to promote bacterial growth, a predetermined quantity of starter bacteria of a desired type or types is desirably introduced into growth chamber 12 through cover 28, or by another similarly effective means, and feed metering device 48 is desirably activated to introduce a desired quantity of suitable pelletized nutrient into fluid 84 in chamber 12. For growth chamber 12 as described herein, the feed is most preferably introduced in portions of about 7.25 grams Referring to FIGS. 1 and 4, when the desired initial quantities of water, starter bacteria and nutrient have been introduced into growth chamber 12 and cover 28 has been secured over the top of chamber 12 by any suitable conventional means, recirculating pump 16 is started and fluid 84 is drawn downwardly through outlet port 26 into inlet 42. After being pressurized by recirculating pump 16, fluid 84, which contains water, bacteria, nutrient and entrained air, is directed back into growth chamber 12 through fluid outlet line 44 and recirculating fluid outlet port 38.

Outlet line 44 and recirculating fluid outlet port 38 are desirably configured and positioned so as to establish a vortex 77 in fluid 84 inside growth chamber 12, substantially as shown in FIG. 4, without excessive foaming. Unlike prior art devices that use subsurface air injection to aerate a bacteria-containing fluid and thereby promote aerobic bacterial growth, the present invention supplies low pressure air to the airspace inside vortex 77 and relies upon the increased surface area contact provided by the swirling vortex to aerate fluid 84 inside growth chamber 12. By aerating fluid 84 in this manner, rather than by bubbling air upwardly through the fluid or by using an eductor disposed in fluid outlet line 44, it is possible to aerate fluid 84 at a molecular level without creating bubbles and excessive foam.

According to a preferred embodiment of the invention, fluid 84 is re-injected tangentially into growth chamber 12. The term "tangentially" is used herein to describe a curved flowpath, initially established in a substantially horizontal direction around inside surface 16 of bacteria growth chamber 12, that diverges from horizontal as it continues around the interior surface of growth chamber 12 and creates a downwardly spiraling vortex 77 in the center of growth chamber 12 above vortex breaker 88 in outlet port 26.

Once the recirculation loop through pump 16 and line 44 has been established as described herein, vortex 77 should extend downwardly substantially the entire distance from the highest liquid level 90 inside growth chamber 12 to vortex breaker element 88, thereby defining a generally conical liquid surface 86 having a compound curvature with its greatest inside diameter occurring at or near top liquid level 90 and its smallest inside diameter occurring at or near outlet port 26 at the bottom of growth chamber 12. Recirculation is continued in this manner for approximately 6 hours while maintaining the temperature of fluid 84 inside bacteria growth chamber 12 within a range of from 16 to about 40° C. (about 60 to about 104° F.), and most preferably between about 29 and about 32° C. (about 84 to about 90° F.) and accompanied by the continuous introduction of inlet water through inlet port 31, the continuous introduction of low pressure air through tip 87, the continuous discharge of fluid through outlet port 36 into fluid discharge line 40, and the continuous flushing of fluid discharge line 40 with water directed into fluid discharge line 40 from flush line 52 at a point disposed below outlet port 36.

After six hours, controller 54 desirably causes feed mechanism 48 to refill feed cup 135 as shown in FIG. 6 with nutrient pellets and to discharge them into bacteria growth chamber 12 through inlet port 34. The same process is desirably continued, with subsequent feedings at six hour intervals, until such time as feed hopper 46 is emptied or, with replenishment of nutrient pellets inside feed hopper 46, until such time as the process is intentionally stopped for periodic inspection and cleaning. Shutdowns for cleaning and maintenance will desirably not be required more often than about once a month, and most preferably about once every two months.

FIG. 8 discloses another embodiment of the invention that uses an electronic controller, timer and solenoid-actuated valves to periodically introduce controlled pulses of water into the bacteria growth chamber and into the bacteria harvesting line to flush harvested bacteria into a use site or accumulation and storage vessel. The controlled cyclical introduction of water into the growth chamber using the embodiment of FIG. 8 can avoid mineral buildup and plugging that might otherwise cause difficulties when using a continuous water drip through a needle valve as described in relation to FIGS. 1, 4 and 5. This can be particularly important where the water is obtained directly from a municipal water supply line and can have a significant mineral content.

Referring to FIG. 8, biomass generator 200 preferably comprises cabinet 201, bacteria growth chamber 214, recirculating pump 224, feed hopper 230, feed metering device 232, air pump 240, electrical transformer 264, timer 266, and controller 268. Biomass generator 200 is preferably self-contained, requiring connection only to a conventional electrical power outlet, water supply line and bacteria harvesting line or receptacle for accumulating bacteria harvested from growth chamber 214. Cabinet 201, comprising top 203, bottom 206, sides 202, 204 and rear 210, and having hinged door 208 disposed on the front side thereof, can be attached to a wall or installed on a stand or table as desired. Door 208 is preferably equipped with a perimeter seal (not shown) to reduce the likelihood of contamination or fluid leakage, and can be provided with a lock to prevent unauthorized access to interior 212 between scheduled service calls. Bottom 206 is desirably watertight and preferably comprises a sump 207 having sufficient volume to capture a liquid volume at least as great as the volume of bacteria growth chamber 214 to prevent escape of water or live bacteria in the event of overflow or leakage from growth chamber 214. Float switch 280 is desirably provided in sump 207 and is connected to controller 268 so as to interrupt power to normally closed, solenoid-actuated water inlet valves 276, 278, in the event of any significant water accumulation in sump 207.

Bacteria growth chamber 214 is similar to that previously described in relation to FIGS. 1, 3 and 4 for growth chamber 12 of biomass generator 10, and preferably comprises substantially cylindrical side wall 216 having top 220 and tapered bottom section 218 with a drain port 222 having a vortex breaker element as previously described in relation to growth chamber 12. Recirculating pump 224 receives bacteria-containing fluid from growth chamber 12 through inlet 282 and discharges pressurized fluid tangentially back into growth chamber 214 through recirculation line 226 and recirculating fluid outlet port 228. Valve 260, which can be manually operated (as shown) or controlled with another electrically actuated solenoid if desired, is provided to redirect fluid discharged from pump 224 through cleanout line 258 into bacteria harvesting line 256 during periodic maintenance on the unit as is described in greater detail below. Valve 260 is desirably configured and installed in recirculation line 226 in such manner that the bacteria-containing liquid flows straight through the valve during normal operation to avoid turbulence, shear and impact that can otherwise adversely affect bacterial growth. Also, cleanout line 258 preferably exits valve 260 at an upward inclination to reduce the likelihood of settling and bacterial buildup that can otherwise occur.

A principal difference between biomass generator 200 as shown in FIG. 8 and biomass generator 10 as previously described in relation to FIGS. 1 through 4 is the structure and operation of the elements that deliver water to bacteria growth chamber 214 and to bacteria harvesting line 256. Referring again to FIG. 8, water entering cabinet 201 through supply line 234 is regulated and distributed through solenoid-actuated valves 276 and 278 into lines 235 and 250, respectively. The water pressure in lines 235 and 250 preferably will not exceed about 30 psi, or the upper range of standard line pressure for municipal water supplies. A conventional flow regulator can be provided to control water pressure in line 234 at about 30 psi if desired.

For a biomass generator 200 having a growth chamber 214 with a volume of about 3 liters, a pulse of approximately 45 ml of water is preferably discharged hourly through valve 276 and line 235 into growth chamber 214. For a typical installation, a pulse of about ¾ second in duration is required to discharge about 45 ml of water. Water is discharged downwardly from line 235 into growth chamber 214 through an inlet port in top 220. A one inch air gap 236 is provided to comply with plumbing codes and a screen or strainer 238, preferably conical, is provided to prevent insects or other contaminants that might gain access to interior 212 of cabinet 201 from entering growth chamber 214.

Water entering growth chamber 214 during the periodic pulses flows downwardly into the vortex formed inside the growth chamber, such vortex having previously been established as described in relation to growth chamber 12 as shown in FIG. 4, and is recirculated through pump 224. As the liquid volume recirculating inside growth chamber 214 increases in this manner, the top level of the liquid rises to the point where bacteria-containing liquid flows outwardly from growth chamber 214 through discharge port 248 into Y-connector 253. Once inside connector 253, the harvested bacteria is flushed downwardly through screen or strainer 254 and larger diameter bacteria harvesting line 256 by water supplied through valve 278 and line 250. The mesh of conical screen or strainer 254 is desirably small enough to capture insects that might gain access to interior 212 of cabinet 201 without unduly impeding the flow of flush water or bacteria down bacteria harvesting line 256.

Flush water is desirably released by solenoid valve 278 in periodic pulses timed to coincide with the discharge of bacteria-containing fluid through port 248 as a result of fresh water being injected periodically into growth chamber 214. The periodic flow of flush water discharged through line 250 into bacteria harvesting line 256 is desirably greater in volume and longer in duration than the flow of inlet water through line 235. According to a preferred embodiment of the invention, the flush cycle is initiated at the same time as, or soon after, the pulsed release of water into growth chamber 214. The flow of flush water is desirably continued for about 30 seconds in order to thoroughly rinse the bacteria out of tee 253 and bacteria harvesting line 256, and into a storage or accumulator vessel (not shown) or directly to the site of an end-use application, as desired. According to a particularly preferred embodiment of the invention, about 1.8 to 2 liters of water are released during the 30 second flow of flush water each hour.

While the introduction of fill and flush water at hourly intervals is preferred, it will be appreciated that longer intervals between successive fill and flush cycles can also be used within the scope of the invention. Thus, for example, it is possible to introduce fill and flush water at intervals ranging from about 1 up to about 15 hours or more if desired. In such circumstances, the length of the pulses will desirably range from about 4.5 to about 12 seconds for fill cycles, and the amount of water released during that time can range from about 185 up to about 500 ml. The length of the associated flush cycles will preferably range from about 15 to about 240 seconds, respectively, with a release of flush water ranging from about 625 ml. to about 10 liters.

Figure 9:
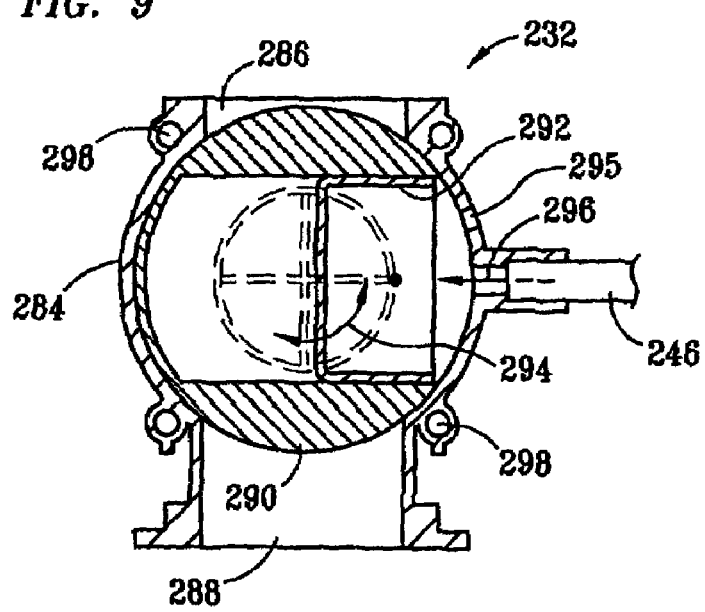
FIG. 9 is cross-sectional elevation view of the lower portion of a preferred nutrient feeder mechanism for use in the invention, showing the feed cup in the intermediate standby position and an air line discharging air into the cup to facilitate drying.

In addition to the water that is introduced hourly into growth chamber 214 during continuous operation of biomass generator 200, nutrient material is desirably added to the liquid medium once every six hours by the use of feed metering device 232. Referring to FIGS. 8 and 9, except as otherwise explained below, feed metering device 232 is preferably made in substantially the same way and functions in substantially the same manner as feed metering device 48 previously described in relation to FIGS. 1, 3-4 and 6-6C. Feed metering device 232 preferably comprises housing 284 having a feed inlet port 286, feed outlet port 288, rotatable core 290 with a transverse cylindrical bore, and feed cup 292 disposed in a stationary position relative to core 290. Threaded apertures 298 are provided in bosses on housing 284 to facilitate attachment of a low voltage DC motor that rotates core 290 either forward or backward, as indicated by arrow 294, in response to signals received from preprogrammed electronic controller 268 as previously described.

Referring to FIG. 8, low pressure air pump 240 functions similarly to air pump 18 as described above and desirably introduces air into the top of bacteria growth chamber 214 through air supply line 242 to maintains a positive pressure of about 0.5 pisg inside growth chamber 214 to help prevent undesirable bacteria from gaining entry into and becoming established inside the chamber. Where cabinet 201 is tightly sealed, it will be appreciated that an air inlet 241 can be provided in side wall 204 to facilitate the introduction of ambient air into air pump 240. One additional preferred feature is disclosed in relation to feed metering device 232 that can also employed with feed metering device 48 if desired. Referring to FIG. 9, a second air outlet line 246 is provided from low pressure air pump 240 to feed metering device 232. Between feed cycles, whenever feed cup 292 is in the "3 o'clock" position, air line 246 continuously discharges air through port 296 into housing 284 of feed metering device 232. This air dries feed cup 292 between feed cycles and forms a dry zone barrier to keep moisture out of the feed pellets and reduce the likelihood of bacterial growth inside feed metering device 232. One or more small vent holes 295 can be provided in housing 284 to permit air introduced through port 296 to exit housing 284.

Although biomass generator 200 is depicted in FIG. 8 with water supply line 234, bacteria harvesting line 256, cleanout line 258, air inlet 241 and power cord 262 all installed through side wall 204 of cabinet 201, it will be appreciated that many other arrangements of these components can be achieved within the scope of the invention. For example, it may be preferable in some cases to place all water lines and connections in one side wall and all electrical components on an opposite wall. In other instances, the preferred placement of such connections may depend upon the location of utilities that are already in place at the use site.

A preferred method and control system for operating biomass generator 200 of the invention to grow bacteria continuously are further described and explained in relation to FIG. 8. Standard AC line current is supplied to biomass generator 200 through power cord 262, and is thereafter distributed as needed by preprogrammed electrical controller 268, which further comprises a transformer module 264, an AC to DC converter module 266, a programmable internal timer, and manual control buttons 270, 272 and 274. Controller 268 desirably supplies 12 volt direct current to the motor of feed metering device 232 and to solenoids 276, 278, and supplies alternating current, preferably stepped down to 18 volts, to air pump 240 and recirculating pump 224. It will be appreciated, however, that air pump 240 and recirculating pump 224 can also be specified to operate on direct current if desired. In general, it is preferred that components inside cabinet 201 be configured to operate on low voltage current to reduce any risk that might otherwise be associated with an inadvertent electrical short inside the cabinet. It will also be appreciated that, if desired, a step-down transformer can be provided externally to cabinet 201 so that only low voltage current enters the cabinet.

During start-up of biomass generator 200, power cord 262 is plugged in to a conventional electrical outlet and button 270 is depressed, causing about two liters of water to be introduced into bacteria growth chamber 214 through solenoid valve 276, after which an initial charge of starter bacteria and pelletized nutrient, preferably totaling about 30 grams, are introduced into bacteria growth chamber 214 by hand. Access to the interior of growth chamber 214 is preferably provided by lifting lid 220.

Recirculating pump 224 and air pump 240 are then activated by depressing button 272 to signal the timer inside controller 268 that biomass generator 200 is in the "charge" mode, during which time the bacteria-containing fluid is recirculated without further addition of water or nutrient for the first 24 hours. After 24 hours, controller 268 automatically advances to the "run" mode. When in the "run" mode, controller 268 of biomass generator 200 periodically and automatically initiates signals to solenoid valves 276, 278 that respectively cause pulses of fresh water to be introduced into bacteria growth chamber 214 and cause flush water to be introduced above Y-connector 253 to flush harvested bacteria into bacteria harvesting line 256. The duration of each pulse and the interval between successive pulses, previously described, can be preprogrammed into controller 268, or biomass generator 200 can be provided with apparatus for setting the intervals and duration for fill water and flush water cycles as desired. In either case, the automatic operation of biomass generator 200 will desirably continue without operator intervention for up to two months following start-up.

Where biomass generator 200 is intended for use inside temperature-controlled buildings wherein the ambient temperatures are within a range that is conducive to rapid bacterial growth, as previously described, it is believed that supplemental heating or cooling of interior 212 of cabinet 201 is not required. However, where the use environment is likely to subject interior space 212 to conditions that are either too hot or cold to promote rapid bacterial growth, the addition of conventional temperature-control devices to cabinet 201 may be needed.

Depending upon the volume of feed hopper 230, it may be necessary to refill the hopper with nutrient pellets more often than every two months, but such replenishment will desirably not require discontinuing the operation of bacteria growth chamber 214 and its ancillary equipment as described above. During continuous operation, bacteria can be harvested and flushed into an accumulator, storage vessel, or the like, or washed through bacteria harvesting line 256 directly to a use site.

Whenever shutdown and cleaning are needed, preferably no more often than once a month and most preferably after two months or longer, the "run" mode can be terminated by depressing button 274. During cleaning, the interior of bacteria growth chamber 214 can be brushed down, the flow restriction element in the bottom of the chamber can be removed and cleaned; screens 238, 254 can be removed and backwashed; and bleach, vinegar or another suitable cleaning compound or reagent can be circulated through the system to remove any bacteria buildup, film or sludge from flow lines, inlet and outlet ports, valves, etc. During cleaning and rinsing of growth chamber 214, valve 260 can be operated manually or otherwise to divert fluid discharged by recirculating pump 224 from line 226 into discharge line 258 and bacteria harvesting line 256. If desired, additional buttons or switches can be provided inside cabinet 201 that can be used to manually cycle valves 276 and 278 open and closed to provide additional fill and flush water during cleaning.

Other examples for possible beneficial application of bacteria in the biomass generated through use of the invention include, without limitation: the decomposition of plant, animal (including poultry and human) waste; treatment of oil and chemical spills; conversion of toxic compounds; digestion of algae; control of insects and fungi; production of active yeast products; food processing; and decomposition of industrial organic waste.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled. Those skilled in the art will also recognize upon reading this disclosure that the physical size, placement and types of bacteria, nutrient, water and air supply devices, control devices, containers and pumps can be varied or modified within the scope of the invention to meet the needs of a particular application.

The invention claimed is:

1. An automated method for growing bacteria continuously and for periodically harvesting the bacteria, the method comprising the steps of:

introducing into a bacteria growth chamber an initial charge of water, starter bacteria and nutrient to form a bacteria-containing fluid;

continuously introducing air into the growth chamber above the bacteria-containing fluid;

continuously recirculating the bacteria-containing fluid by withdrawing fluid through a bottom outlet in the growth chamber; pressurizing the fluid in a recirculation pump; and discharging the pressurized fluid back into the growth chamber in a tangential direction to establish a vortex of bacteria-containing fluid inside the growth chamber;

periodically introducing pulses of fill water into the growth chamber, the pulses being spaced apart at predetermined intervals and each lasting for a predetermined duration;

periodically harvesting bacteria through a bacteria harvesting port disposed slightly above the vortex in the growth chamber, said periodic harvesting occurring at times corresponding to the pulsed introduction of fill water into the growth chamber;

periodically introducing a flow of flush water into a drain line communicating with the bacteria harvesting port, the flow of flush water commencing substantially at the same time as the pulses of fill water and being of sufficient quantity and duration to flush bacteria received through the bacteria harvesting port down the drain line to a use site or accumulation vessel; and periodically introducing predetermined quantities of nutrient into the growth chamber to replenish nutrients consumed by the growing bacteria.

2. The method of claim 1 wherein the temperature of the recirculating bacteria-containing fluid is maintained within a range of from about 16° C. to about 40° C.

3. The method of claim 2 wherein the temperature of the recirculating bacteria-containing fluid is maintained with a range of from about 29° C. to about 32° C.

4. The method of claim 1 wherein the pulses of fill water occur at intervals ranging from about one to about 15 hours apart.

5. The method of claim 1 wherein the duration of the pulses of fill water range from about 4.5 to about 12 seconds.

6. The method of claim 1 wherein the bacteria growth chamber has a volume of about 3 liters.

7. The method of claim 6 wherein the volume of fill water introduced into the bacteria growth chamber during the pulses ranges from about 185 to about 500 ml.

8. The method of claim 6 wherein the volume of flush water introduced into the bacteria harvesting line during each period ranges from about 625 to about 10,000 ml.

9. The method of claim 6 wherein about 29 grams of nutrient are preferably introduced into the bacteria growth chamber daily, in four equal increments of about 7.25 grams each, with each increment being introduced approximately 6 hours apart.

10. The method of claim 1 wherein the introduction of flush water occurs at intervals ranging from about one to about 15 hours apart.

11. The method of claim 1 wherein the flow of flush water continues for a duration ranging from about 15 to about 240 seconds.

12. The method of claim 1 wherein nutrient feed is introduced into the bacteria growth chamber every six hours.

13. An automated method for continuously growing and harvesting bacteria, the method comprising the steps of:

introducing into a bacteria growth chamber an initial charge of water, starter bacteria and nutrient to form a bacteria-containing fluid;

continuously introducing air into the growth chamber above the bacteria-containing fluid;

continuously recirculating the bacteria-containing fluid by withdrawing fluid through a bottom outlet in the growth chamber; pressurizing the fluid in a recirculation pump; and discharging the pressurized fluid back into the growth chamber in a tangential direction to establish a vortex of bacteria-containing fluid inside the growth chamber;

continuously introducing fill water into the growth chamber;

continuously harvesting bacteria through a bacteria harvesting port disposed slightly above the vortex in the growth chamber;

continuously introducing a flow of flush water into a drain line communicating with the bacteria harvesting port, the flow of flush water being sufficient quantity to flush bacteria received through the bacteria harvesting port down the drain line to a use site or accumulation vessel; and periodically introducing predetermined quantities of nutrient into the growth chamber to replenish nutrients consumed by the growing bacteria.

14. The method of claim 13 wherein the temperature of the recirculating bacteria-containing fluid is maintained within a range of from about 16° C. to about 40° C.

15. The method of claim 14 wherein the temperature of the recirculating bacteria-containing fluid is maintained with a range of from about 29° C. to about 32° C.

16. The method of claim 13 wherein nutrient feed is introduced into the bacteria growth chamber every six hours.

17. The method of claim 13 wherein about 29 grams of nutrient are preferably introduced into the bacteria growth chamber daily, in four equal increments of about 7.25 grams each, with each increment being introduced approximately 6 hours apart.

* * * * *